United States Patent [19]

Punja

[11] 4,091,110
[45] May 23, 1978

[54] INSECTICIDAL ESTERS

[75] Inventor: Nazim Punja, Wokingham, England

[73] Assignee: Imperial Chemical Industries Limited, London, England

[21] Appl. No.: 786,394

[22] Filed: Apr. 11, 1977

[30] Foreign Application Priority Data

Apr. 12, 1976 United Kingdom ............. 14761/76

[51] Int. Cl.² .................. A01N 9/20; A01N 9/24; C07C 69/76; C07C 121/75
[52] U.S. Cl. .................. 424/304; 260/465 D; 424/308; 560/105
[58] Field of Search ............ 260/465 D; 560/105; 424/304, 308

[56] References Cited

U.S. PATENT DOCUMENTS 3,979,519  9/1976  Punja ..................... 424/304
3,996,244  12/1976  Fujimoto et al. ............ 560/105 X Primary Examiner—Dolph H. Torrence
Attorney, Agent, or Firm—Cushman, Darby & Cushman

[57] ABSTRACT

Compounds of the formula

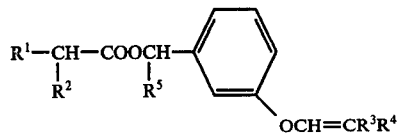

wherein $R^1$ represents a branched lower alkyl radical; $R^2$ represents a phenyl group optionally substituted with halogeno or lower alkyl radicals; $R^3$ and $R^4$ represent halogeno radicals; and $R^5$ represents a hydrogen atom or the cyano radical. These compounds are useful as insecticides.

9 Claims, No Drawings

INSECTICIDAL ESTERS

This invention relates to novel esters, to processes for preparing them, to compositions comprising them, and to methods of combating insect pests using them.

Accordingly the present invention provides esters of formula:

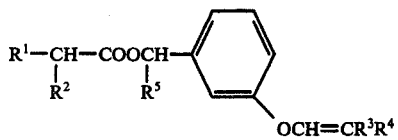
(I)

wherein $R^1$ represents a branched lower alkyl radical; $R^2$ represents a phenyl group optionally substituted with halogeno or lower alkyl radicals; $R^3$ and $R^4$ represent halogeno radicals; and $R^5$ represents a hydrogen atom or the cyano radical.

By the term "halogeno" as used herein is meant fluoro, chloro or bromo; and by the term "lower alkyl" is meant alkyl containing up to four carbon atoms.

In a preferred form the invention provides compounds wherein $R^1$ is the isopropyl group, and $R^2$ is phenyl sustituted in the para-position with chloro or methyl. $R^3$ and $R^4$ are preferably both chloro, and $R^5$ is preferably cyano.

It will be readily appreciated that the compounds of the invention as set out hereinabove are described without reference to their stereochemical nature. Thus the above formula does not differentiate between the geometrical isomers which are possible nor does it differentiate between the various stereoisomeric forms which may be present, and the present invention includes within its scope all such geometric and optical steroisomers. Thus the term "compound" as used herein in relation to esters of the invention refers both to an individual isomer in isolation, and to mixtures of isomers thereof e.g. racemic mixtures, diastereoisometric mixtures.

The following compounds are typical examples of compounds according to the invention.

3-(2,2-dichlorovinyloxy)benzyl (±)-2-(4-chlorophenyl)-3-methylbutyrate (hereinafter referred to as Compound 1).

3-(2,2-dichlorovinyloxy)benzyl (±)-2-(4-tolyl)-3-methylbutyrate (hereinafter referred to as Compound 2).

(±)-α-cyano-3(2,2-dichlorovinyloxy)benzyl (±)-2-(4-chlorophenyl)-3-methylbutyrate.

(±)-α-cyano-3(2,2-dichlorovinyloxy)benzyl (±)-2-(4-tolyl)-3-methylbutyrate.

The invention compounds may be prepared by several different processes. Thus a compound of formula:

(II)

optionally in the form of a metal salt thereof, may be reacted with a compound of formula:

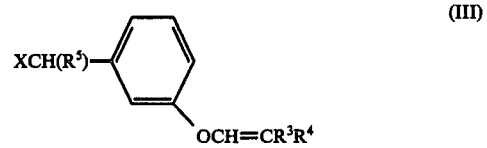
(III)

wherein X is a halogen atom, preferably a chlorine or bromine atom, and $R^1$, $R^2$, $R^3$, $R^4$ and $R^5$ have any of the meanings given hereinabove, or with the quaternary salt derived from compound III and a tertiary amine, e.g. a trialkylamine such as triethylamine. Alternatively a compound of formula:

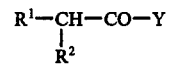

may be reacted with a compound of formula:

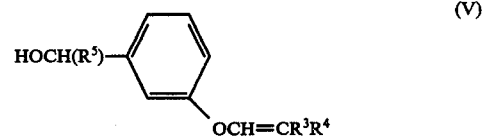
(V)

wherein Y is a halogen atom, preferably a chlorine atom, and $R^1$, $R^2$, $R^3$, $R^4$ and $R^5$ have any of the meanings given hereinbefore.

In another process the invention esters may be obtained by the process of transesterification wherein the mixture of a simple ester (e.g. a lower alkyl ester such as the methyl or ethyl ester) of the acid of formula II and the alcohol of formula V is heated, optionally in a solvent or diluent, and preferably in the presence of a base (e.g. a lower alkoxide such as sodium methoxide or ethoxide).

These processes may in some cases be carried out by heating the reactants together in the absence of a diluent and/or a base, but preferably a solvent or diluent and a base is present. Suitable solvents include, for example, non-hydroxylic materials such as aliphatic ketones (e.g. acetone), dimethylformamide, dimethylsulphoxide, sulpholane, acetonitrile and tetrahydrofuran. Of these an aliphatic ketone such as, for example acetone is particularly preferred. Hydroxylated solvents, for example, methanol and ethanol, may be used in certain circumstances when the presence of the hydroxyl group does not interfere with the process of the reaction. Suitable bases include sodium hydride (although not when a hydroxylated solvent or diluent is used), alkali metal carbonates, such as potassium carbonate and alkali metal hydroxides such as potassium hydroxide. The temperature at which the reaction may be carried out will depend upon the choice of reactants, solvent or diluent and base. When acetone and potassium carbonate are used the reaction generally takes place at the ambient temperature. Higher temperatures, up to 100° C, may be employed when other bases are employed. A typical process consists of dissolving or suspending the reactants in a solvent in the presence of a base. After allowing a period of time for the reaction to occur the product may be isolated by the removal of any insoluble portion by filtration and evaporation of the filtrate. The product may be purified by distillation under reduced pressure, or by a suitable chromatographic technique.

The compounds of formula III and formula V which are used in the above processes for the preparation of the invention esters may be prepared by the following processes.

Thus a compound of formula III wherein $R^5$ is hydrogen may be prepared from a compound of the formula:

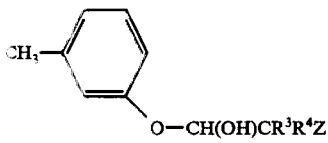

(VI)

by subjecting them to chemical or electrochemical reductive dehydrohalogenation to give a compound of formula:

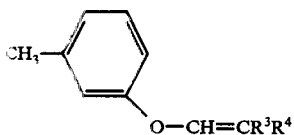

(VII)

and thereafter halogenating the methyl group of compound VII to produce the required compound of formula III. Z in formula VI is a halogen radical, and is preferably the same halogen radical as that represented by $R^3$ and $R^4$.

Compounds of formula VI may be prepared by a method analogous to that of von Hesse and Moll, J. Prakt. Chemie, 1974, 316(2), 304 in which anhydrous chloral or bromal is reacted with m-cresol in the presence of an acyl halide.

The electrochemical reduction procedure may be carried out in organic solvents, for example lower alcohols, such as methanol or ethanol, cyclic ethers such as dioxan or tetrahydrofuran, aliphatic ketones such as acetone or cyclohexanone, or mixtures of these solvents with water or water containing strong mineral acids such as sulphuric, hydrochloric or phosphoric acids.

The reduction is believed to occur principally at the cathode with a high hydrogen overvoltage, for example a mercury, lead amalgam or lead cathode. The reaction can be conveniently carried out in a cell fitted with a ceramic or glass fritted diaphragm, a stirrer, a working electrode and a reference electrode. The process may be adapted for continuous production of the required product by use of a solvent system with which the product of the reaction may be extracted, for example methylene chloride.

The metallic reductive dehydrohalogenation may be carried out with a suitable reducing medium such as zinc dust and acetic acid.

Halogenation of the compounds of formula VII may conveniently be carried out with the aid of a source of positive halogen, for example an N-haloimide such as N-bromosuccinimide, or N-chlorosuccinimide. The compounds of formula V wherein $R^5$ is hydrogen may conveniently be prepared from the corresponding compounds of formula III by, for example, treating them with an alkali metal hydroxide, or alternatively converting them to the corresponding tosylate (p-toluenesulphonate) and subjecting the tosylate to hydrolysis.

Compounds of formula III wherein $R^5$ is hydrogen may be converted to the corresponding compounds wherein $R^5$ is a cyano radical by the process of treating a compound of formula III wherein $R^5$ is hydrogen with a source of cyanide ion, e.g. an alkali metal cyanide such as sodium cyanide, and thereafter subjecting the compound of formula:

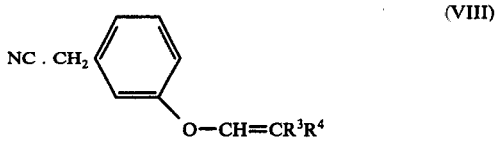

(VIII)

thus produced to further halogenation. The reaction with cyanide may conveniently be performed in a polar aprotic solvent such as dimethylformamide, at an elevated temperature in the range 50° to 100° C. The halogenation step may conveniently be performed in the manner outlined above for the preparation of compound of formula III wherein $R^5$ is hydrogen. The compounds of formula V wherein $R^5$ is cyano may be obtained from the compounds of formula III where $R^5$ is cyano by analogous processes to those set out above for the corresponding compounds where $R^5$ is hydrogen.

A preferred method for the preparation of compounds of formula V where $R^5$ is cyano is however based on a different approach in which a compound of formula VII is selectively oxidised to a compound of formula:

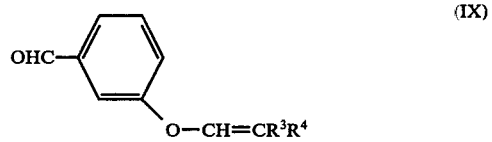

(IX)

and this compound if then converted to its cyanohydrin by reaction with hydrogen cyanide, or, preferably, via the bisulphite compound, with cyanide ion (e.g. sodium cyanide). An alternative process for preparing compound IX involves the oxidation of compound V where $R^5$ is hydrogen with aluminium isopropoxide and acetone under the conditions of the Oppenauer reaction.

As stated above the invention esters of formula I are useful as insecticides, and are most conveniently used as such when formulated into compositions. In another aspect therefore the invention provides insecticidal compositions which comprise as an active ingredient an invention ester of formula I in association with agriculturally and horticulturally acceptable diluent or carrier materials.

In a preferment of this aspect of the invention the active ingredient is selected from amongst the specifically named esters of the invention set out hereinabove.

The compositions are for use in agriculture or horticulture but the type of composition used in any instance will depend upon the particular purpose for which it is to be used.

The compositions may be in the form of granules or powders comprising the active ingredient and a solid diluent or carrier. The compositions may also be in the form of liquid preparations to be used as dips or sprays which are generally aqueous dispersions or emulsions.

The compositions to be used as sprays may also be in the form of aerosols wherein the formulation is held in a container under pressure in the presence of a propellant such as fluorotrichloromethane or dichlorodifluoromethane.

For agricultural or horticultural purposes, an aqueous preparation containing between 0.0001% and 1.0% by weight of the active ingredient or ingredients may be used.

The compositions of the present invention may, if desired, also comprise in addition to a compound of the present invention, at least one other biologically active ingredient, for example, an insecticide or a fungicide. They may also comprise a synergist of the type useful in synergising the activity of pyrethroids type insecticides.

In use, the invention compounds or compositions may be used to combat insects in a variety of ways. Thus the insects themselves, or the locus of the insects or the habitat of the insects is treated with a compound or a composition according to the invention.

The invention also provides a method of treating plants to render them less susceptible to damage by insects, which comprises treating the plants, or the seeds, corms, bulbs, tubers, rhizomes or other propagative parts of the plants, or the medium in which the plants are growing with a compound or composition according to the invention.

Thus the compounds of the invention are toxic towards a wide variety of insect and other invertebrate pests, including for example the following: *Dysdercus fasciatus, Blatella germanica, Alphis fabae, Musca domestica, Megoura viceae, Pieris brassicae, Aedes aegypti, Plutella maculipennis*.

The invention is illustrated by the following Examples.

EXAMPLE 1

This example illustrates the preparation of 3(2,2-dichlorovinyloxy)benzyl 2-p-tolyl-3-methylbutyrate, of formula:

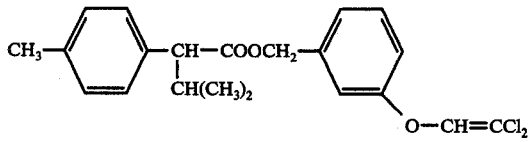

A mixture of 3(2,2-dichlorovinyloxy)benzyl bromide (2.5 g, 60% pure), 2-p-tolyl-3-methylbutyric acid (1.0 g), anhydrous potassium carbonate (0.72 g) and dry acetone (25 ml) was stirred for 1 hour at the ambient temperature, and then at 45° C for 3 hours, followed by a further period of 18 hours at the ambient temperature. After removal of the solid portion by filtration, the filtrate was washed with saturated sodium bicarbonate solution, and then with water, and dried over anhydrous magnesium sulphate. The oil obtained after removal of the volatile portion by evaporation under reduced pressure was subjected to preparative thin layer chromatography using silica gel on glass and as eluent a mixture of 1 part by volume of chloroform with 4 parts by volume of petroleum ether (boiling range 60° to 80° C), to yield 3(2,2-dichlorovinyloxy)benzyl 2-p-tolyl-3-methylbutyrate, identified by nuclear magnetic resonance, infra red and mass spectrometry. Found m/e+ 392, $C_{21}H_{22}H_3Cl_2$ requires 393.

EXAMPLE 2

This example illustrates the preparation of 3(2,2-dichlorovinyloxy)benzyl bromide.

(a) Preparation of 1(3-tolyloxy)-2,2,2-trichloroethyl acetate

To a solution of anhydrous chloral (37.0 g) in dry ether (125 ml) was added meta-cresol (27.0 g) and the mixture was stirred at the ambient temperature for 20 minutes, after which it was cooled to 10° C and a solution of triethylamine (25.25 g) in dry ether (100 ml) was slowly added. Acetyl chloride (20.0 g) was then carefully added to the stirred mixture and stirring was continued for 1 hour. The insoluble material was removed by filtration and the filtrate dried over anhydrous magnesium sulphate. After removal of the ether by evaporation under reduced pressure the residual oil was distilled under high vacuum and the fraction boiling at 132°–135°/0.5 mm Hg collected. Infra-red and nuclear magnetic spectroscopic analysis indicated that this was 1(3-tolyloxy)-2,2,2-trichloroethyl acetate.

(b) Preparation of 3-tolyl 2,2-dichlorovinyl ether (i) By a metallic reductive dehydrohalogenation method. 1(3-tolyloxy)-2,2,2-trichloroethyl acetate (14.2 g) was dissolved in glacial acetic acid (40 ml) and zinc dust (3.6 g) was slowly added to the solution with stirring at the ambient temperature. The temperature rose to 60° C in response to the exothermic reaction which occurred, after which the mixture was heated at 50°–60° C for 4 hours. The mixture was filtered and the filtrate poured in an excess of water and extracted with chloroform. The extracts were washed twice with water, with saturated sodium bicarbonate solution, and finally with water. After drying the chloroform extracts over anhydrous magnesium sulphate, the solvent was removed by evaporation under reduced pressure and the residual oil distilled to yield crude 3-tolyl 2,2-dichlorovinyl ether, collected as a fraction boiling at 92°–95° C/0.3 mm, which was redistilled and the fraction boiling at 84° C/0.2 mm Hg collected.

(ii) By an electrochemical reductive dehydrohalogenation method. 1(3-tolyloxy)-2,2,2-trichloroethyl acetate (15.8 g), concentrated sulphuric acid (98% w/v, 9.8 g) and methanol (220 ml) was charged into an electrolytic cell, which was surrounded by a cooling bath set to maintain the temperature at about 15° C, and fitted with a cylindrical diaphragm, stirrer, reference electrode (SCE) and a working electrode. The cathode was a lead plate (surface area about 40 cm²). Using a current density in the range 5 to 10 mA/cm² the reaction was conducted in the potential range −1100 to 1700 mV (SCE). When reduction was completed the cathodic electrolyte was neutralised with caustic soda and extracted with methylene chloride, the extracts dried over anhydrous sodium sulphate and evaporated to yield a residue of crude 3-tolyl 2,2-dichlorovinyl ether.

(c) Preparation of 3(2,2-dichlorovinyloxy)benzyl bromide

3-Tolyl 2,2-dichlorovinyl ether (12.2 g) was dissolved in carbon tetrachloride (75 ml), and N-bromosuccinimide (12.0 g) and a trace of wet benzoyl peroxide added, and the mixture refluxed for 3 hours. After filtration the solvent was evaporated from the filtrate, and the residue dissolved in ether and extracted with 1% w/v sodium hydroxide solution. The ethereal solution was dried over anhydrous magnesium sulphate, the solvent removed by evaporation under reduced pressure, and the residual oil distilled to yield a fraction boiling at 150° C/0.5 mm Hg. This fraction was shown by NMR to contain about 65% of the required product together with about 30% of unchanged starting material, the remainder being a small proportion of the dibromomethyl compound.

EXAMPLE 3

This example illustrates the preparation of 3(2,2-dichlorovinyloxy)benzyl alcohol.

A mixture of 3(2,2-dichlorovinyloxy)benzyl bromide (2.8 g), sodium p-toluene sulphonate (2.0 g) and methanol (20 ml) is warmed to 50° C for 1 hour, after which water (20 ml) and toluene (20 ml) is added with agitation. The toluene layer is separated, washed with water and concentrated by evaporation of the solvent under reduced pressure. The concentrate is then added dropwise to a 15% (w/v) aqueous solution of potassium hydroxide (100 ml) and the mixture warmed to 60° C for 1 hour, cooled to the ambient temperature and extracted with a mixture of toluene (10 ml) and methyl iso-butylketone (10 ml), the extracts dried over anhydrous magnesium sulphate and the solvents evaporated under reduced pressure to yield 3(2,2-dichlorovinyloxy)benzyl alcohol as a residual pale yellow oil.

EXAMPLE 4

This Example illustrates the conversion of 3(2,2-dichlorovinyloxy)benzaldehyde to its cyanohydrin, via the bisulphite compound.

To a stirred solution of sodium metabisulphite (3.2 g) in a mixture of water (5.2 ml) and methanol (5.2 ml) at the ambient temperature is added 3(2,2-dichlorovinyloxy)benzaldehyde (2.0 g). After 30 minutes the white precipitate which forms is collected by filtration, washed with cold methanol and dried to yield the bisulphite compound of 3(2,2-dichlorovinyloxy)-benzaldehyde (2.5 g). This is suspended in water (5 ml) and to it is added a solution of sodium cyanide (0.4 g) in water (5 ml) at the ambient temperature. The mixture is stirred for 2 hours and then extracted with diethyl ether (2 × 10 ml). The extracts are combined, washed with water (2 × 10 ml), dried over anhydrous magnesium sulphate and evaporated under reduced pressure to yield the cyanohydrin of 3(2,2-dichlorovinyloxy)-benzaldehyde as a yellow oil.

EXAMPLE 5

The activity of a compound of the invention was tested against a variety of insect and other invertebrate pests. The compound was used in the form of a liquid preparation containing 0.1% by weight of the compound except in the tests with *Aedes aegypti* where the preparations contained 0.01% by weight of the compound. The preparations were made by dissolving the compound in a mixture of solvents consisting of 4 parts by volume of acetone and 1 part by volume of diacetone alcohol. The solutions were then diluted with water containing 0.01% by weight of a wetting agent sold under the trade name "LISSAPOL" NX until the liquid preparations contained the required concentration of the compound. "Lissapol" is a Trade Mark.

The test procedure adopted with regard to each pest was basically the same and comprised supporting a number of the pests on a medium which was usually a host plant or a foodstuff on which the pests feed, and treating either or both the pests and the medium with the preparations.

The mortality of the pests was then assessed at periods usually varying from one to three days after the treatment.

The results of the tests are given below in Table I. in this table the first column indicates the name of the pest species. Each of the subsequent columns indicates the host plant or medium on which it was supported, the number of days which were allowed to elapse after the treatment before assessing the mortality of the pests, and the results obtained for the compound expressed in integers which range from 0–3, where 0 represents less than 30% kill
1 represents 30 – 49% kill
2 represents 50 – 90% kill
3 represents over 90% kill A dash (-) in Table I indicates that no test was carried out.

In Table I 'contact test' indicates that both the pests and the medium were treated and 'residual test' indicates that the medium was treated before infestation with the pests.

TABLE I

| PEST SPECIES | SUPPORT MEDIUM | NO. OF DAYS | COMPOUND NO. 2 |
|---|---|---|---|
| *Aphis fabae* (black aphids) | Broad Bean | 2 | 2 |
| *Megoura viceae* (green aphids) | Broad Bean | 2 | 2 |
| *Aedes aegypti* (mosquito adults) | Plywood | 1 | 2 |
| *Musca domestica* (houseflies - contact test*) | Milk/ sugar | 2 | 3 |
| *Plutella maculipennis* (diamond back moth, larvae) - contact test | Mustard | 2 | 2 |
| *Pieris brassicae* (cabbage white caterpillars - contact test | Cabbage | 2 | 3 |

EXAMPLE 6

This Example illustrates a dusting powder which may be applied directly to plants or other surfaces and comprises 1% by weight of Compound no. 1 and 99% by weight of talc.

EXAMPLE 7

25 Parts by weight of Compound no. 2, 65 parts by weight of xylene and 10 parts of an alkyl aryl polyether alcohol ('Triton' X-100; 'Triton' is a Trade Mark) were mixed in a suitable mixer. There was thus obtained an emulsion concentrate which can be mixed with water to produce an emulsion suitable for use in agricultural applications.

EXAMPLE 8

10 Parts by weight of Compound no. 2, 10 parts of an ethylene oxide-nonylphenol condensate ('Lissapol' NX; 'Lissapol' is a Trade mark) and 80 parts by weight of diacetone alcohol were thoroughly mixed. There was thus obtained a concentrate which, on mixing with water, gave an aqueous dispersion suitable for application as a spray in the control of insect pests.

EXAMPLE 9

This Example illustrates the preparation of 3(2,2-dichlorovinyloxy)benzaldehyde.

3(2,2-Dichlorovinyloxy)benzyl bromide (2.5 g) was carefully added to a stirred solution of hexamethylene tetramine (2.1 g) in carbon tetrachloride (20 ml) at the ambient temperature. After 5 minutes the precipitate was collected by filtration and washed with acetone. The solid thus obtained was added to aqueous acetic acid solution (50% by weight, 16 ml) and the mixture refluxed for 1 hour. A mixture of water (16 ml) and concentrated hydrochloric acid (4.5 ml) was then added and the mixture refluxed for a further 15 minutes. After cooling the mixture was extracted with chloroform, the extracts washed with water (twice), dried over anhydrous magnesium sulphate and the solvent removed by evaporation under reduced pressure to yield a residue of substantially pure 3(2,2-dichlorovinyloxy)benzaldehyde, identification of which was confirmed by infrared and nuclear magnetic resonance spectroscopy.

I claim:

1. An ester of formula:

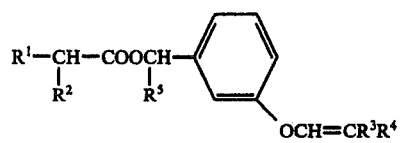

wherein $R^1$ is branched alkyl of up to four carbon atoms, $R^2$ is phenyl, or halo- or alkyl-substituted phenyl containing up to 4-carbon atoms in the alkyl moiety, $R^3$ and $R^4$ are chloro, and $R^5$ is hydrogen or cyano.

2. An ester according to claim 1 wherein $R^1$ is isopropyl and $R^2$ is 4-chlorophenyl or 4-tolyl.

3. An ester according to claim 2 wherein $R^5$ is cyano.

4. 3-(2,2-Dichlorovinyloxy)benzyl ($\pm$)-2-(4-chlorophenyl)-3-methylbutyrate.

5. 3-(2,2-Dichlorovinyloxy)benzyl ($\pm$)-2-(4-tolyl)-3-methylbutyrate.

6. ($\pm$)-$\alpha$-Cyano-3-(2,2-dichlorovinyloxy) ($\pm$)-2-(4-chlorophenyl)-3-methylbutyrate.

7. ($\pm$)-$\alpha$-Cyano-3-(2,2-dichlorovinyloxy) ($\pm$)-2-(4-tolyl)-3-methylbutyrate.

8. A composition for use in combating insect pests at a locus which comprises an insecticidally effective amount of an ester according to claim 1 in association with an agriculturally and horticulturally acceptable diluent or carrier material.

9. A method of combating insect pests at a locus which comprises treating the locus with an insecticidally effective amount of a composition according to claim 8.

* * * * *